(12) United States Patent
McLean

(10) Patent No.: US 7,878,999 B2
(45) Date of Patent: Feb. 1, 2011

(54) BRACE FOR THE PROXIMAL TIBIOFIBULAR JOINT

(76) Inventor: Allison McLean, 8230 Mountainview Drive, Whistler, British Columbia (CA) V0N 1B8

( * ) Notice: Subject to any disclaimer, the term of this patent is extended or adjusted under 35 U.S.C. 154(b) by 807 days.

(21) Appl. No.: 11/449,592

(22) Filed: Jun. 9, 2006

(65) Prior Publication Data

US 2006/0282029 A1    Dec. 14, 2006

Related U.S. Application Data

(60) Provisional application No. 60/689,063, filed on Jun. 10, 2005.

(51) Int. Cl.
*A61F 5/00* (2006.01)
*A61F 13/00* (2006.01)

(52) U.S. Cl. .............. 602/23; 602/5; 602/60; 602/62

(58) Field of Classification Search .......... 602/20, 602/26, 60–64, 5, 23, 27; D24/190–192, D24/64; 2/24, 22
See application file for complete search history.

(56) References Cited

U.S. PATENT DOCUMENTS

| 3,496,573 | A | * | 2/1970 | Pope et al. .......... 2/161.6 |
|---|---|---|---|---|
| 5,277,697 | A | | 1/1994 | France et al. |
| 5,829,055 | A | * | 11/1998 | Collins et al. .......... 2/22 |
| 5,865,782 | A | * | 2/1999 | Fareed .......... 602/62 |
| 6,077,242 | A | | 6/2000 | Falk et al. |
| 6,080,124 | A | * | 6/2000 | Falk et al. .......... 602/26 |
| 6,149,617 | A | * | 11/2000 | McNally et al. .......... 602/62 |
| 6,540,711 | B2 | | 4/2003 | Cox |
| 6,796,951 | B2 | | 9/2004 | Freeman et al. |

OTHER PUBLICATIONS

Trainer's Choice Knee Braces—Levy Patellar Strap—pages from website http://www.trainerschoice.on.ca/trainers/index.htm printed Feb. 28, 2005.

* cited by examiner

*Primary Examiner*—Kim M Lewis
(74) *Attorney, Agent, or Firm*—Bereskin & Parr LLP/S.E.N.C.R.L., s.r.l.

(57) ABSTRACT

Various embodiments of an orthopedic appliance for bracing and supporting a joint are described herein. The orthopedic appliance includes a first support portion and a second support portion with surfaces partially facing one another, and a force application element. In use, the first and second support portions are located on opposing sides of an outer portion of the joint and, in conjunction with the force application element, apply partially opposing forces to the joint.

20 Claims, 11 Drawing Sheets ively on
BRACE FOR THE PROXIMAL TIBIOFIBULAR JOINT

REFERENCE TO RELATED APPLICATION

This application claims priority from U.S. provisional patent application having Ser. No. 60/689,063 filed on Jun. 10, 2005.

FIELD

Various embodiments are described herein for an orthopaedic appliance for bracing joints such as the proximal tibiofibular joint (i.e. TF joint).

BACKGROUND

Different types of orthopaedic appliances for bracing the joints of the human system are known. The primary purpose of such appliances or orthoses is to provide stability and support for a joint that has become mechanically unstable due to some form of pathology.

In the simplest form orthoses are known that substantially immobilize a joint so as to facilitate the healing of injured tissue. In more complex forms functional orthoses are known that attempt to restore normal or near normal stability and joint kinematics to a joint that has some form of residual laxity. Such appliances can also provide prophylaxis for repaired or reconstructed ligaments.

The mechanical designs of functional orthoses vary greatly. Orthoses can be either static or dynamic in design. Dynamic orthoses allow movement of a joint while they control excessive moment in order to protect the joint from further injury. A dynamic orthosis employs active restraint, or preload, to a joint for the purpose of resisting translation of the bones at the joint interface. A static orthosis rests passively on the limb until forces that tend to create instability occur.

The knee is one of the largest and most complex joints in the human system. It relies almost entirely on soft tissue structures in the form of ligaments, tendons, joint capsule and cartilage for mechanical stability. Because of its complexity and reliance on soft tissue for mechanical stability the knee is susceptible to injury.

The problem with bracing any joint is that the brace must be affixed on the skin. All designers and manufacturers of orthoses must operate under this constraint. Because of this limitation, little resistance is available in known orthoses with which to oppose tangential forces. In addition, the interposed soft tissue between an orthosis and the structures of a joint prevent a direct mechanical interface with the supporting structures of a limb. An important consideration in the design of any orthosis is the ability to effectively transfer load to the affected joint.

While many conventional orthoses have been developed for the knee complex, there are little if any orthoses specifically intended to brace the proximal tibiofibular joint. The reason for this is that the role of the proximal tibiofibular joint in pathologies of the knee and ankle has received little recognition in the medical literature.

The proximal tibiofibular joint is an arthrodial plane joint consisting of a tibial facet located on the posterolateral aspect of the rim of the tibial condoyle, and a fibular facet located on the medial proximal aspect of the fibula. The facets of the joint are oriented in the posteromedial plane. Translations of the facet of the proximal fibula with the facet of the proximal tibia in this plane are either posteromedial or anterolateral.

The anterior and posterior ligaments of the proximal tibiofibular joint act in a synergistic relationship to maintain translations and rotations of the head of the fibula with the lateral tibial facet within their normal range of motion. In this capacity, the anterior and posterior ligaments apply forces to the proximal fibula that are balanced when the joint is in a neutral position. The proximal tibiofibular joint is in a neutral position in weight bearing characterised by erect, quiet standing.

Other stabilizing structures of the proximal tibiofibular joint are: 1) the interossesus membrane which is comprised of a fibrous sheet running the length between the fibula and the tibia; 2) a strong fibrous capsule which surrounds the joint and is attached to the margins of the articular facets and the lateral collateral ligament, which in turn originates from the lateral epicondyle of the femur and inserts at the apex of the fibula; and 3) the biceps femoris muscle which in turn inserts on the apex of the fibula around the insertion of the lateral collateral ligament.

The anterior ligament of the proximal tibiofibular joint is comprised of short, thick fibrous bands that angle obliquely and superomedially from the anterior aspect of the head of the fibula to the anterior aspect of the lateral tibial condoyle. The posterior ligament is comprised of a single thin band that angles obliquely and superomedially from the posterior aspect of the fibula to the posterior aspect of the lateral tibial condoyle. Differences in the thickness and therefore, the relative strength of the anterior and posterior ligaments in combination with differences in the angles in which the ligaments are oriented relative to the plane of the facets of the proximal tibiofibular joint create asymmetric loading of the proximal tibiofibular joint. The weaker structure of the posterior ligament predisposes it to damage from the excessive force associated with knee flexion in weight bearing.

Ligaments are designated by their function: i.e. reinforcing ligaments for the joint capsule, restrictive ligaments to restrict joint movements or guiding ligaments for guiding joint movements. The anterior and posterior ligaments of the proximal tibiofibular joint provide both a stabilizing effect on the joint and a guiding effect on the joint arthrokinematics. The force applied by these ligaments guides the proximal tibiofibular joint in rotation and in the glide and translation that occurs during knee and ankle joint motion.

The normal translations of the proximal fibula at the proximal tibiofibular joint are anterolateral, posteromedial, superior and inferior glide. Recent evidence shows that the surfaces of the tibiofibular joint translate as much as 5 millimetres with each other in flexion and extension of the knee joint. The normal rotations of the fibula are internal or external.

One-sixth of body weight may be considered to be a static load applied to the fibula during weight bearing with the remaining five-sixths being borne by the tibia. The proximal to middle one third of the fibula has greater tensile strength than the femur. Therefore, in weight bearing the fibula acts to dissipate torsional stresses and direct compressive loads.

In weight bearing cases, the proximal tibiofibular joint translates anterolaterally with a lateral rotation of the torso with reference to the associated limb and posteromedially with medial rotation of the torso with reference to the associated limb. As the talocrural joint dorsiflexes as in a standing squat position, the proximal fibula translates superiorly and anterolaterally while rotating externally in relation to its neutral position. When rising up on the toes, the proximal fibula translates posteromedially and inferiorly, and rotates internally with plantarflexion of the talocrural joint.

In non-weight bearing cases, the proximal fibular head translates posteromedially with knee extension and anterolaterally with knee flexion. During dorsiflexion of the talocrural joint, the proximal fibula translates anterolaterally while rotating externally. During plantarflexion of the talocrural joint, the proximal fibular head translates posteromedially while rotating internally.

The distal tibiofibular joint moves in response to movement of the proximal fibula. Due to the articulation of the medial surface of the distal fibula with the talus, excessive movement due to ligament pathology in the form of laxity, or restricted movement will affect the talocrural joint. Positional faults in the proximal and/or distal fibula create undue strain on the anterior talofibular, calcanealfibular and posterior talofibular ligaments. This alters the arthrokinematics of the talocrural joint.

The common peroneal nerve passes posteriorly over the head of the proximal fibula. It gives off genicular branches; the lateral sural cutaneous nerve and the sural communicating nerve, which innervate the tibiofemoral joint and the proximal tibiofibular joint. The common peroneal nerve is the only nerve that attaches to a bone, in this case, the fibular head, via a retinaculum. The common peroneal nerve then divides into the superficial and deep peroneal nerves, which are motor nerves to the muscles of the foot and ankle. Oval apertures in the interossesus membrane allow for passage of the anterior tibial and peroneal vessels. Research has shown that an external force greater than 30 mm Hg applied to soft tissue structures will impede arteries, veins and the vaso vasorum of the peripheral nerve.

Studies have demonstrated surgery can often be avoided with effective early treatment of instability of a joint. Therefore, the comfort, effectiveness and ease of use of an orthosis play a significant role in the success or failure of any therapy.

SUMMARY

In one aspect, at least one embodiment described herein provides an orthopaedic appliance for bracing and supporting a joint, the orthopaedic appliance comprising a support member including a base, a first support portion and a second support portion, the first and second support portions partially facing one another; a securing member for securing the support member to the joint; and, an attachment element for attaching the securing member to the support member. In use, the first and second support portions are located on partially opposing sides of an outer portion of the joint and, in conjunction with the securing member, apply partially opposing forces to the joint to substantially mimic the synergistic action of the ligaments associated with the joint.

In another aspect, at least one embodiment described herein provides an orthopaedic appliance for bracing and supporting a joint. The orthopaedic appliance comprises a first support portion and a second support portion with surfaces partially facing one another, and a force application element. In use, the first and second support portions are located on opposing sides of an outer portion of the joint and, in conjunction with the force application element, apply partially opposing forces to the joint.

In another aspect, at least one embodiment described herein provides an orthopaedic appliance for bracing and supporting a joint. The orthopaedic appliance comprises a first support portion with a first surface; a second support portion with a second surface partially facing the first surface; a force application element coupled to the first and second support portions and adapted to apply forces to the first and second support portions; and a resistance member coupled to the force application element and at least one of the first and second support portions, the resistance member being adapted to change at least one of the forces applied to the first and second support portions. In use, the first and second support portions are located on opposing sides of an outer portion of the joint and, in conjunction with the force application element, apply partially opposing forces to the joint.

BRIEF DESCRIPTION OF THE DRAWINGS

For a better understanding of the various embodiments described herein and to show more clearly how they may be carried into effect, reference will now be made, by way of example only, to the accompanying drawings in which.

DETAILED DESCRIPTION

Figure 1:
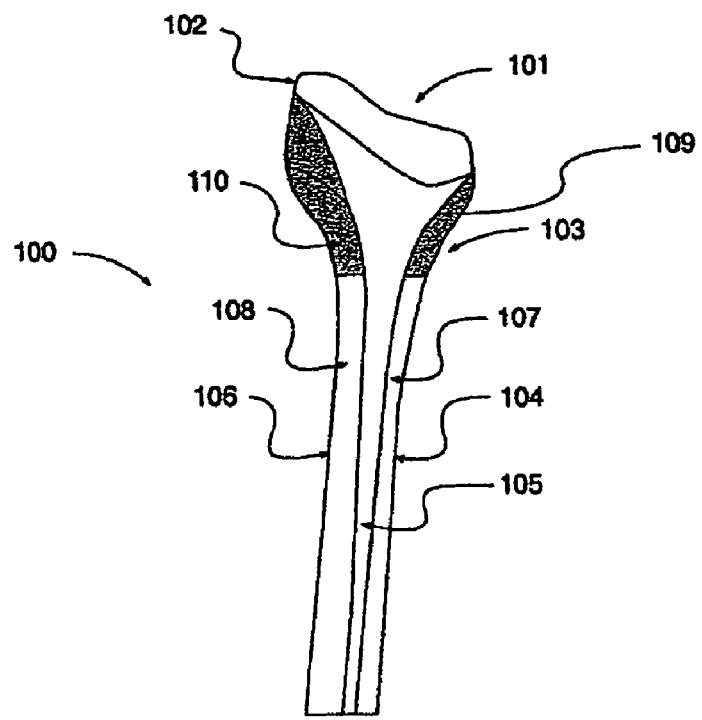
FIG. 1 is a lateral sagittal plane view of the right proximal fibula with its anatomic surfaces shown for reference to the various embodiments described herein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements. In addition, numerous specific details are set forth in order to provide a thorough understanding of the various elements described herein. However, it will be understood by those of ordinary skill in the art that these embodiments may be practiced without these specific details. In other instances, well-known methods, procedures and components have not been described in detail so as not to obscure the embodiments described herein. It should further be understood that the term orthosis has a similar meaning to the terms orthopaedic appliance and brace.

In one aspect, various embodiments described herein provide an orthopaedic appliance designed to brace and support the proximal tibiofibular joint in a manner that substantially mimics the synergistic function of its anterior and posterior ligaments while allowing for substantially normal arthrokinematics of the joint. This reduces the residual laxity in the proximal tibiofibular joint that is typically due to some form of pathology. Accordingly, the form of the various embodiments of the orthopaedic appliance for the proximal tibiofibular joint and the materials of which it is comprised are selected to comply with shape of the anterolateral and posterolateral aspects of the head and neck of the proximal fibula. In order to effectively transfer load to these aspects of the proximal fibula, the contact surface of the orthosis are shaped so as to displace adjoining soft tissue while minimizing discomfort to the user. In addition, the material of the orthosis in contact with the skin surface is selected to not cause irritation or chafing of the interposed tissue. The various embodiments of the orthosis described herein mimic the synergy of the soft tissue restraints, and the synergy of the anterior and posterior ligaments thereby allowing for substantially normal arthrokinematics of the proximal tibiofibular joint.

Another feature of the various embodiments described herein is that when the force required to restore integrity to the proximal tibiofibular joint is applied with the minimal compressive force required to control the translations and rotations of the proximal fibula, the force applied by the various orthoses described herein will not unduly compress the joint or the nerves associated with the joint. That is to say, these braces will not load the fibula against the tibia in a manner that prevents substantially normal arthrokinematics. Compressing the proximal tibiofibular joint in a manner that disrupts normal arthrokinematics can result in a compression injury of the joint.

The various orthotic embodiments described herein also provide an adjustment means or element for independently adjusting the forces applied to the anterior and posterior aspects of the proximal tibiofibular joint. This is important in situations where it may be necessary to compensate for significant deviations in the vectors of force applied to the proximal tibiofibular joint by its ligaments and the vectors of force applied to the proximal tibiofibular joint by the structures of the orthosis, which act as quasi ligaments. In addition, the adjustment element can at least partially compensate for a pathology of the proximal tibiofibular joint that disrupts the normal relationship of the anterior and posterior ligaments as they relate to their ability to return the joint to a neutral position.

FIG. 1 is a lateral sagittal plane view of the right proximal fibula generally shown at 100. Its anatomical surfaces are shown for reference to the application of the various orthoses described herein.

The head of the fibula 100 is generally shown at 101. The apex of the head 101 of the fibula 100 is shown at 102. The neck of the fibula 100 is generally shown at 103. The anterior aspect of the fibula 100 is shown at 104. The lateral aspect of the fibula 100 is shown at 105. The posterior aspect of the fibula 100 is shown at 106. The anterolateral aspect of the fibula 100 is shown at 107. The posterolateral aspect of the fibula 100 is shown at 108.

The shaded area at 109 shows the approximate primary area of contact of the various embodiments of the orthoses described herein on the anterolateral aspect 107 of the proximal fibula 100 through the interposed soft tissue. The shaded area at 110 shows the approximate primary area of contact of the various embodiments of the orthoses on the posterolateral aspect 108 of the proximal fibula 100 through the interposed soft tissue.

The proximal fibular head 101 and neck 103 are structurally prominent on the lateral aspect of the distal knee joint. They are easily detected by surface palpation, as their form is usually visually discernable under the surface of the cutaneous soft tissue.

Figure 2:
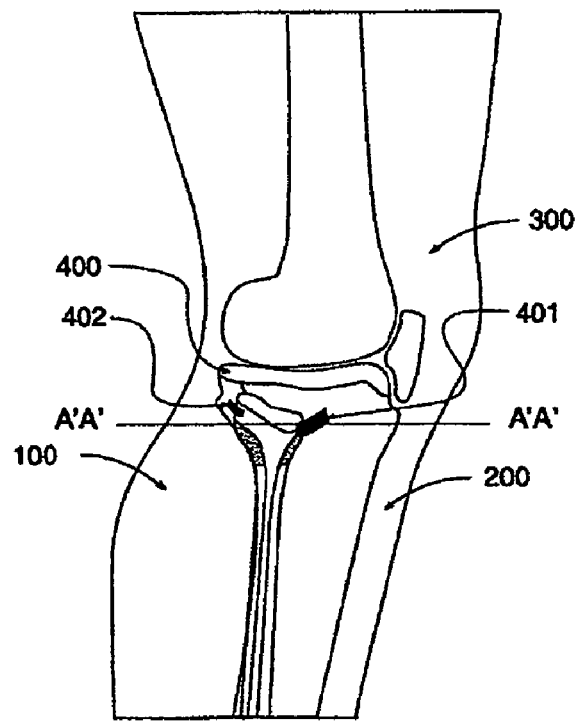
FIG. 2 is a lateral sagittal plane view of the right proximal tibiofibular joint showing a portion of the distal thigh and proximal leg.

FIG. 2 is a lateral view of the right knee joint with the proximal tibiofibular joint generally shown at 400. The proximal fibula is generally shown at 100. The proximal tibia is generally shown at 200. The distal femur is generally shown at 300. Unless otherwise indicated, all figures show the proximal tibiofibular joint in its neutral position. When the sum of the opposing forces applied to the joint by its supporting structures, in particular the anterior and posterior ligaments, is zero, the proximal fibula joint is in a neutral position. The proximal tibiofibular joint is in a neutral position in weight bearing characterised by erect, quiet standing.

Figure 3:
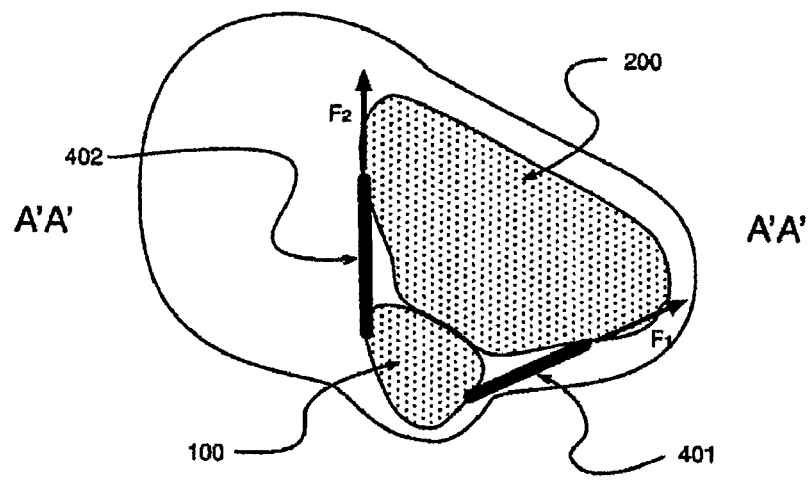
FIG. 3 is a coronal plane section of the right proximal tibiofibular joint indicated in FIG. 2 showing its anterior and posterior ligaments.

FIG. 3 is proximal view of the coronal section A'A'-A'A' as indicated in FIG. 2 of the right proximal tibiofibular joint. The right proximal fibula is shown at 100. The right proximal tibia is shown at 200. Although anatomically outside the plane of section A'A'-A'A', the anterior ligament 401 and the posterior ligament 402 are shown for reference to the operation of various orthotic embodiments described herein. Depending on morphological variations, the anterior ligament 401 is substantially oriented in an anteromedial plane while the posterior ligament is substantially oriented in a plane that can be aligned posteromedial to lateromedial.

Arrows emanating from the anterior ligament 401 and the posterior ligament 402 indicate the vectors of the resultant forces, F1 and F2 applied by the ligaments that restrain the proximal fibula 100 in translation and rotation with reference to the facet of the proximal tibia 200. The net effect of the anterior and posterior ligaments 401, 402 working in a synergistic relationship is to exert a pull on the anterior and posterior aspects of the proximal fibula 100 that act to maintain the integrity of the proximal tibiofibular joint while allowing for normal arthrokinematics.

Figure 4:
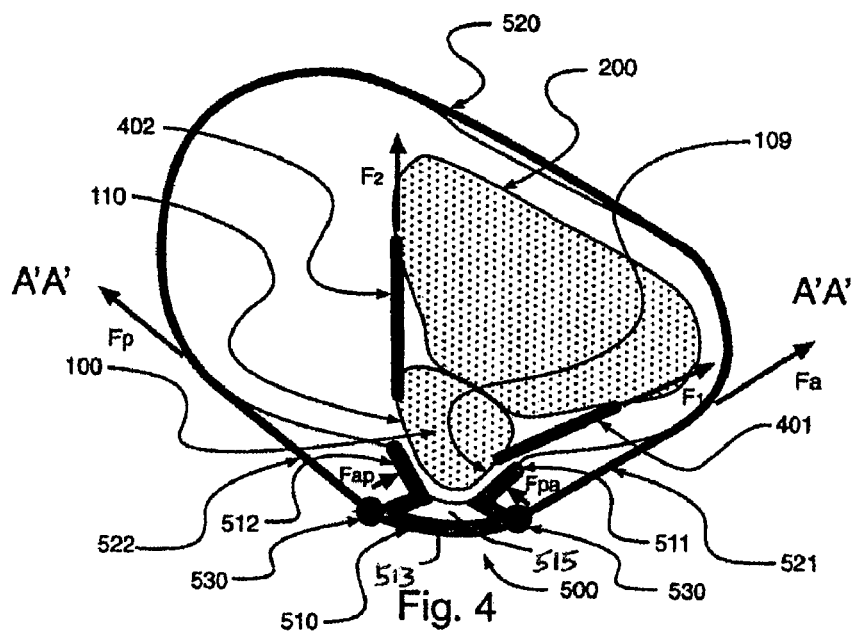
FIG. 4 is a similar view to that shown in FIG. 3 along with a schematic representation of one exemplary embodiment of an orthosis.

FIG. 4 is the same view of the proximal tibiofibular joint as in FIG. 3 except that in FIG. 4 a schematic of an exemplary embodiment of an orthosis is generally shown at 500.

The orthosis 500 includes a support member 510 and a securing member 520. The securing member 520 may also be referred to as a force application means or element. The support member 510 has a first support portion 511, a second support portion 512 and a recessed portion 513 defining a void 515 between the first support portion 511 and the second support portion 512. The first support portion 511 is situated anterolaterally with respect to the proximal fibula 100. The recessed portion 513 is situated laterally with respect to the proximal fibula 100. The second support portion 512 is situated posterolaterally with respect to the proximal fibula 100. When the securing member 520 tensions the support member 510 against the proximal fibula 100, the first support portion 511 applies a posteromedially acting force to the interposed tissue between the skin and the anterolateral aspect 109 of the proximal fibula 100 signified by the arrows while the second support portion 512 applies an anteromedially acting force to the interposed tissue between the skin and the posterolateral aspect 110 of the proximal fibula 100. The void 515 defined by the recessed portion 513 accommodates the lateral aspect of proximal fibula 100.

The support member 510 of orthosis 500 is secured in position on the proximal tibiofibular joint 400 by the securing member 520 that is attached to the anterior and posterior aspects of support member 510 with an attachment means or element 530. The anterior aspect 521 of the securing member 520 is associated with the anterior ligament 401 of the proximal tibiofibular joint 400. The posterior aspect 522 of the securing member 520 is associated with the posterior ligament 402 of the proximal tibiofibular joint 400. The anterior and posterior aspects, 521 and 522 of securing member 520 are respectively affixed anteriorly to the first support portion 511 of support member 510 and posteriorly with respect to the second support portion 512 of support member 510 to secure the support member 510 of orthosis 500 in position on the proximal tibiofibular joint 400 of the leg of a wearer.

The anterior aspect 521 of securing member 520 applies an anteromedially directed force Fa to the anterior aspect of the support member 510 of orthosis 500. The posterior aspect 522 of the securing member 520 applies an opposing posteromedially directed force Fp to the posterior aspect of the support member 510 of orthosis 500. Arrows indicate the direction of the force vectors Fa and Fp applied to support member 510 by portions of the securing member 520 of orthosis 500. Accordingly, the first and second support portions 511 and 512 are on partially opposing sides of the proximal tibiofibular joint 400 and apply, in conjunction with the securing member 520, partially opposing forces Fap and Fpa to the proximal tibiofibular joint 400 in a manner that substantially mimics the synergy of the anterior and posterior ligaments of the proximal tibiofibular joint The forces Fa and Fp applied to the proximal TF joint (represented by force vectors Fap and Fpa) act in opposition to each other and thus substantially mimic the forces applied to the proximal tibiofibular joint F1 and F2 by its anterior and posterior ligaments.

Accordingly, portions of the securing member 520 act as quasi-ligaments. Since it is not possible to affix the ends of the securing member 520 directly to the anterolateral and posterolateral aspects of the proximal fibula in the same manner as its anterior and posterior ligaments without invasive procedures, the forces applied to the support member 510 by the securing member 520 are externally transferred to the proximal fibula on the aspects of the proximal fibula opposite each end of the securing member. For instance, the anterior aspect 521 of the securing member 520 acts as the anterior ligament 401 in combination with the transfer of force at the posterior aspect of the support member 510. The same is true of the posterior aspect 522 of the securing member 520 for acting as the posterior ligament 402. To alter the nature of forces transferred to the proximal fibula one may alter the connection of the securing member 520 to the support member 510. For example, if some form of pathology has compromised the anterior ligament 401, the load may be increased on the posterior aspect of the support member 510 by altering the mechanics on the anterior aspect of the support member 510. This will increase the force that acts to resist posterior translation which is similar to the action taken by the ligament.

When connected to the anterior and posterior aspects of the support member 510 of orthosis 500 and tensioned about the leg, the anterior aspect 521 of the securing member 520 exerts a pull Fa on the anterior aspect of the support member 510 of orthosis 500 that causes the second support portion 512 of the support member 510 to apply an anteromedial push on the posterolateral aspect 110 of the proximal fibula 100. Similarly, the posterior aspect 522 of the securing member 520 exerts a posteromedial pull Fp on the posterior aspect of the support member 510 that causes the first support portion 511 of orthosis 500 to apply a posteromedial push on the anterolateral aspect 109 of the proximal fibula 100. Therefore, the combined effect of the force applied to the anterolateral aspect 109 and the posterolateral aspect 110 of the proximal fibula 100 by orthosis 500 substantially mimics the combined forces applied by the anterior ligament 401 and the posterior ligament 402 of the proximal tibiofibular joint 400. Compression components of forces Fa and Fp maintain the support member 510 in position on the proximal fibula 100 while shear components of forces Fa and Fp allow the support member 510 to control translations and rotations of the proximal tibiofibular joint 400.

Figure 5:
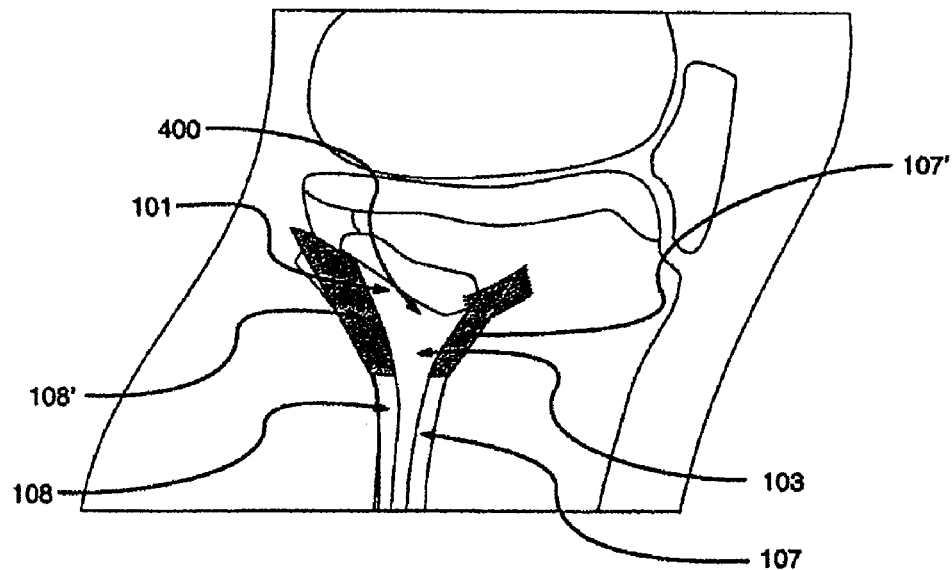
FIG. 5 is a lateral sagittal plane view of the right proximal tibiofibular joint showing the anterolateral and posterolateral primary skin contact surfaces made with the various orthotic appliances described herein.

FIG. 5 is a lateral sagittal plane view of the right proximal tibiofibular joint generally shown at 400 showing the approximate shape and positions of the contact areas of the first support portion 511 and the second support portion 512 of the support member 510 of orthosis 500 during use. The first and second support portions 511 and 512 of the support member 510 of orthosis 500 are shaped and configured so as to apply force primarily to the general contours 107' and 108' respectively of the anterolateral and posteromedial aspects 107 and 108 of the head and neck 101 and 103 of the proximal fibula 100 through the interposed soft tissue. Due to the asymmetric anatomical shape of the head 101 of the proximal fibula 100, the second support portion 512 of the support member 510 of orthosis 500 may be larger in both the vertical dimension and surface area compared to the first support portion 511 to ensure correct positioning and alignment of the support member 510 in relation to the proximal tibiofibular joint 400.

The shape of the support member 510 of orthosis 500 captures the head 101 and neck 103 of the proximal fibula 100 in a manner that allows the proximal tibiofibular joint 400 to move within its normal range of motion under the influence of the securing member 520 that secures the support member 510 of orthosis 500 in place about the calf of the wearer. This is because the shape of support member 510 of orthosis 500, in combination with the securing member 520, applies guiding forces similar to the anterior and posterior ligaments of the proximal tibiofibular joint. Thus under the influence of securing member 520 and the first and second support portions 511 and 512 of support member 510 and the void 515 defined by the recessed portion 513 of support member 510, the orthosis 500 allows for substantially normal arthrokinematics of the proximal tibiofibular joint.

Figure 6:
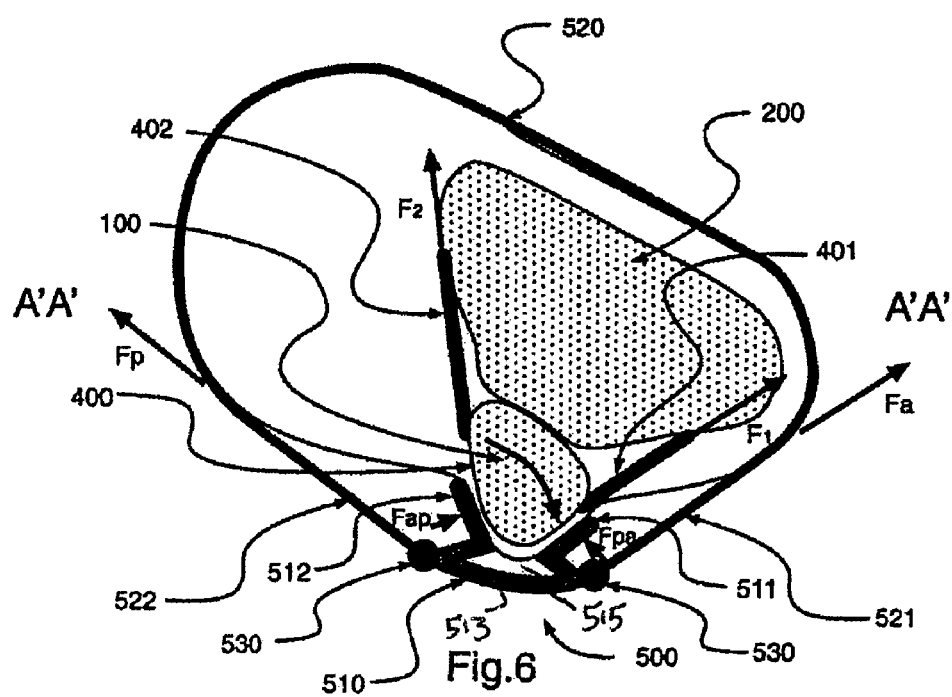
FIG. 6 is a coronal plane sectional view showing the operation of the orthosis of FIG. 4 when the proximal fibula has translated anterolaterally and rotated externally in relation to the position shown in FIG. 4.

FIG. 6 shows the same view as FIG. 4 except that the proximal fibula has translated anterolaterally and rotated externally with reference to its neutral position with the facet of the proximal tibia. Without considering the orthosis 500, these movements have resulted in a change in force applied by the anterior ligament 401 and the posterior ligament 402 from that of the neutral position of the proximal tibiofibular joint 400. The changes in force in the anterior ligament 401 and the posterior ligament 402 of the proximal tibiofibular joint 400 set up forces that tend to restore the joint 400 to its neutral position. The re-centering effect is the primary purpose of the anterior and posterior ligaments 401 and 402 of the proximal tibiofibular joint 400.

Still referring to the motion shown in FIG. 6, now considering the orthosis 500, in a similar fashion to the actions of the anterior ligament 401 and the posterior ligament 402 for this particular translation of the proximal fibula, the pull on the posterior aspect 522 of the securing member 520 has increased while the pull on the anterior aspect 521 of the securing member 520 has decreased. This can be understood by looking at the gaps between these portions of the securing member 520 and the anterior and posterior regions of the tibiofibular joint 400. The changes in force in the posterior aspect 522 and the anterior aspect 521 of the securing member 520 results in corresponding changes in the push exerted on the proximal fibula by the first support portion 511 of the orthosis 500 and the second support portion 512 of the orthosis 500. The end result is that the changes in force in the anterior aspect 521 and posterior aspect 522 of the securing member 520 of the orthosis 500 set up forces which tend to restore the proximal tibiofibular joint 400 to its neutral position. Accordingly, in this situation the orthosis 500 mimics the action of the anterior and posterior ligaments 401 and 402 of the proximal tibiofibular joint 400.

Figure 7:
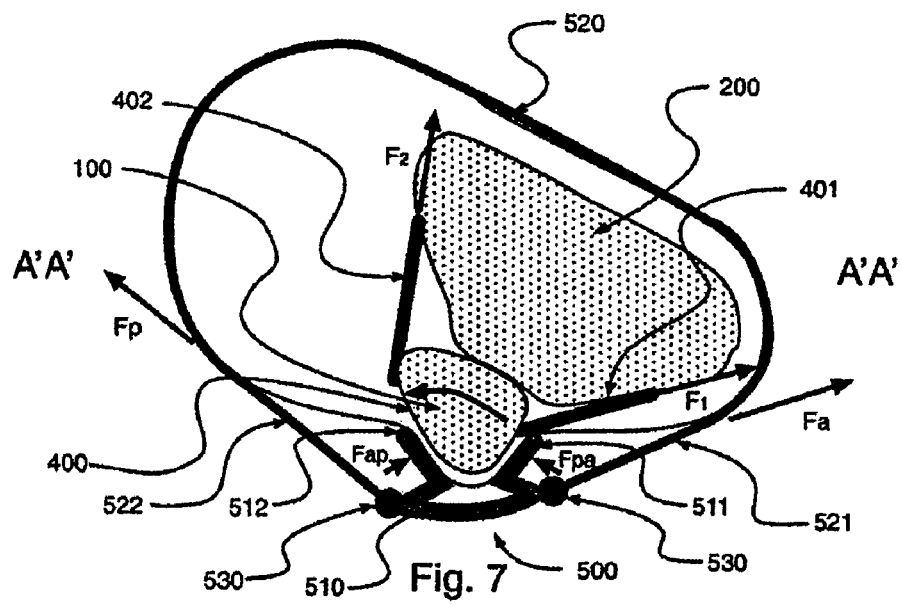
FIG. 7 is a coronal plane sectional view showing the operation of the orthosis of FIG. 4 when the proximal fibula has translated posteromedially and rotated internally in relation to the position shown in FIG. 4.

FIG. 7 shows the same view as FIG. 4 except that the proximal fibula has translated posteromedially and rotated internally with reference to its neutral position with the facet of the proximal bbia. Without considering the orthosis 500, these movements have resulted in a change in force in the anterior ligament 401 and the posterior ligament 402 from that of the neutral position of the proximal tibiofibular joint 400 shown in FIG. 4. The changes in force in the anterior ligament 401 and the posterior ligament 402 of the proximal tibiofibular joint 400 set up forces that tend to restore the joint to its neutral position.

Now considering the same movement when the orthosis 500 is being used, in a similar fashion, the pull on the posterior aspect 522 of the securing member 520 has increased while the pull on the anterior aspect 521 of the securing member 520 has decreased. The changes in force in the posterior aspect 522 and the anterior aspect 521 of the securing member 520 results in corresponding changes in the push exerted on the proximal fibula by the first support portion 511 of the support member 510 of orthosis 500 and the second support portion 512 of the support member 510 of orthosis 500. The end result is that the changes in force in the anterior aspect 521 and posterior aspect 522 of the securing member 520 of the orthosis 500 set up forces which tend to restore the proximal fibiofibular joint to its neutral position. Accordingly, in this situation the orthosis 500 once again mimics the action of the anterior and posterior ligaments 401 and 402 of the proximal tibiofibular joint 400.

In addition to the aforementioned anterolateral and posteromedial translations, the proximal fibula 100 undergoes proximal and distal translations with certain joint movements. The general structure of the orthosis 500 also accommodates such translations. Translations and rotations of the proximal fibula 101 in relation to the facet of the tibia 200 are accompanied by corresponding changes in the shape and cross sectional area of the mass of the calf muscle of the leg. These changes in the calf muscle assist the action of the orthosis 500 by increasing the tension of the securing member 520 during translations and rotations of the proximal tibiofibular joint 400 and thus the recentering force applied to the proximal fibula by the first and second support portions 511 and 512 of the support member 510.

Figure 8:
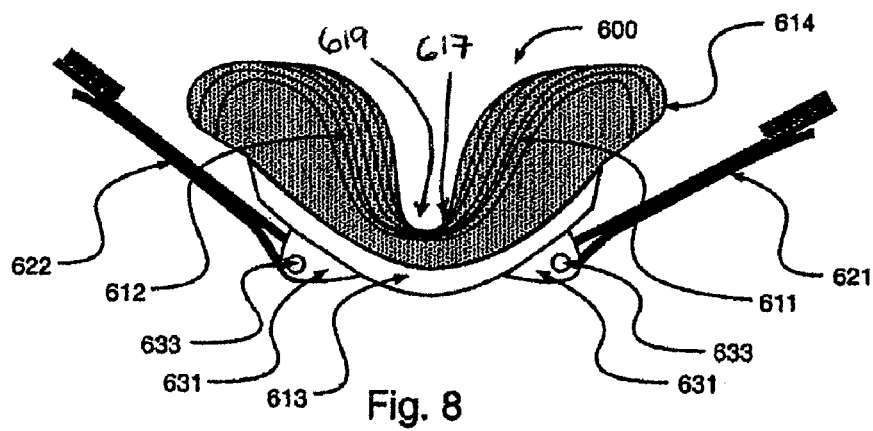
FIG. 8 is a proximal coronal plane view of another exemplary embodiment of an orthosis.
Figure 9:
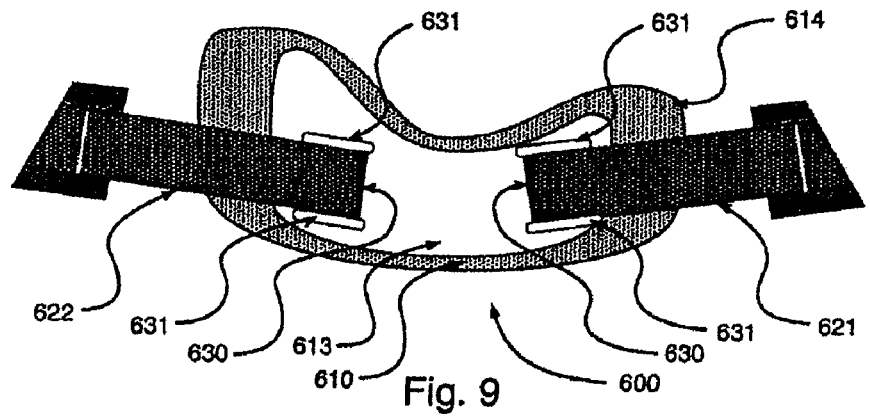
FIG. 9 is a lateral sagittal plane view of the orthosis of FIG. 8.

Referring now to FIGS. 8 and 9, shown therein are coronal plane and sagittal plane views, respectively, of another exemplary embodiment of an orthosis 600. The orthosis 600 includes a support member 610 comprised of an outer component 613 and an inner component 614. The outer component 613 forms a rigid or semi-rigid structure or chassis for the support member 610 of the orthosis 600. The inner component 614 is the skin contact medium of the support member 610 of the orthosis 600 and includes first and second support portions 611 and 612 and a recessed portion 617 defining a void 619 therebetween. The outer and inner outer components 613 and 614 have a concave upper surface and a convex lower surface, with the ends of the inner and outer components extending upwardly.

Figure 10A:
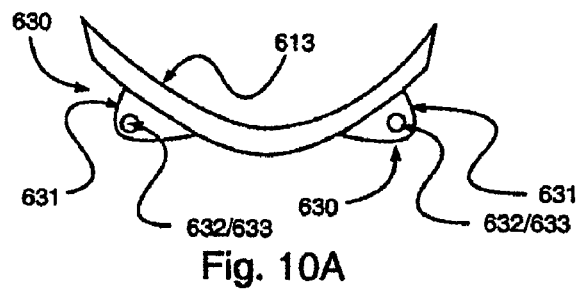
FIG. 10A is a proximal coronal plane view of an outer component of the orthosis of FIG. 8 as configured for the right proximal tibiofibular joint of a wearer.
Figure 10B:
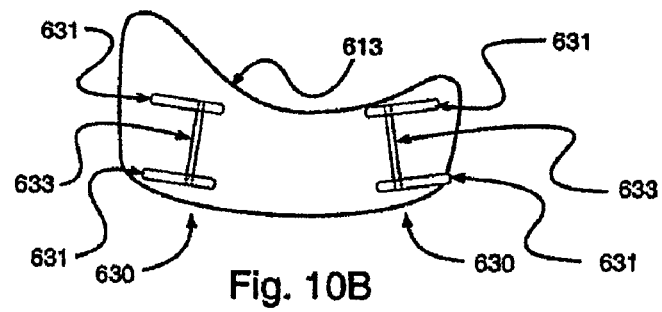
FIG. 10B is a lateral sagittal plane view of the outer component of the orthosis of FIG. 8 as configured for the right proximal tibiofibular joint of a wearer.

Referring now to FIGS. 10A and 10B, shown therein are proximal coronal plane and sagittal plane lateral views showing the outer component 613. The outer component 613 may be made from rigid or semi-rigid materials such as carbon fiber or nylon, for example. The outer component 613 includes an attachment means or element shown generally at 630 to connect the support member 610 to the securing member. In this exemplary embodiment, four flanges 631 may be integral with the outer component 613 or rigidly affixed to it. Pins 633 are mounted in pairs in receiving holes 632 (not shown in this figure) in the flanges 631 located at the anterior and posterior aspects of the support member 610 as fixations means for attaching the securing member 620 to the support member 610. The flanges 631 may be angled slightly proximally to allow the securing member 620 to sit on the crown of the calf muscle just below the knee joint of the wearer. This orientation of the securing member 620 reduces the tendency for the orthosis 600 to migrate distally in use. In an alternative embodiment, alternative means such as receiving slots may be located in the outer component 613 to fix or hold the securing member 620 in place. The proximal margin of the posterior half of the both the outer component 613 and inner component 614 extend proximally above the anterior half of the support member 610 and are also greater in surface area in order to conform to the asymmetric shape of the apex 102 of the head 101 of the proximal fibula 100.

Figure 10C:
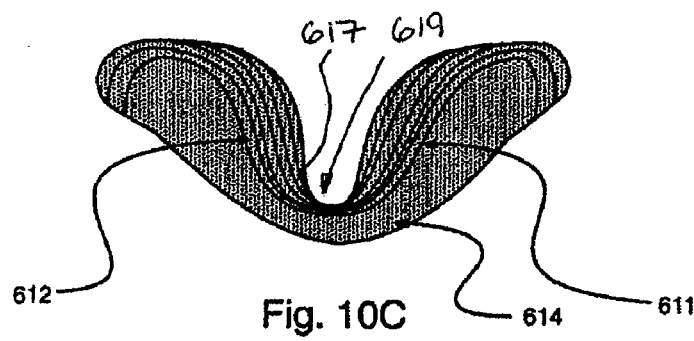
FIG. 10C is a proximal coronal plane view of an inner component of the orthosis of FIG. 8 as configured for the right proximal tibiofibular joint of a wearer.
Figure 10:
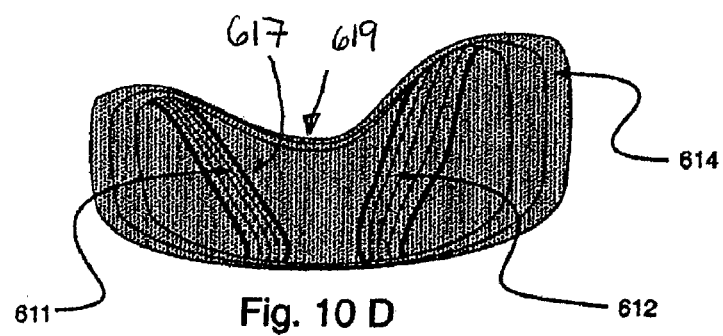
FIG. 10D is a sagittal plane view of the medial or skin surface of the inner component of the orthosis of FIG. 8 as configured for the right proximal tibiofibular joint of a wearer.

Referring now to FIGS. 10C and 10D shown therein are proximal plan and inverted side views, respectively, of the inner component 614 of the orthosis 600. The inner component 614 can be made from material that has quasi-hydraulic qualities while still being progressively resistive to general deformation. This resistive quality aids in the transfer of shear force to the TF joint 400. With co-molding technology it may be possible to combine two materials to make the inner component 614 and the outer component 613 such that the inner component 614 provides the skin surface side with quasi-soft tissue characteristics while retaining the ability to maintain the required shape.

In some embodiments, the inner component 614 may be made from a viscoelastic gel type material or a similar material with quasi-hydraulic characteristics. A viscoelastic gel matrix may include glycerin, water and acrylic polymer as a cross-linked polysaccharide. Other materials that may be used include rubber, neoprene and foam. These can all provide a degree of surface adaptation as well as absorb energy from ground reaction shock. But such materials may be too stiff or lack sufficient density to rebound after each vibrational shock wave in order to absorb the next shock wave. Thus such materials may be used but are suboptimal since they may allow vibrational energy to be transferred to the proximal tibiofibular joint, which may result in pain and dysfunction for the user.

Viscoelastic gel type materials provide superior performance in terms of the ability to absorb energy from ground reaction force, especially energy in the form of shock since the dampening characteristics of viscoelastic gel matrix type formulations are superior to other materials used for this purpose. In addition, viscoelastic gel matrix is one of the few materials capable of dissipating secondary shock waves from vibration. The quasi-hydraulic characteristics of viscoelastic gel matrices may also provide superior performance as an interface medium for the skin surface. Accordingly, the inner component 614 can be made from a viscoelastic gel type material.

It should further be noted that the skin side of the inner component 614 of the support member 610 of the orthosis 600 may be shaped so as to cup the fibular head and neck of the proximal fibula 100 anteriorly and posteriorly. Accordingly, the anterior and posterior inner portions of the inner component may be shaped differently with respect to one another to accommodate the different shapes of the anterior and posterior portions of the proximal tibiofibular joint 400. For instance, the posterior portion or second support portion 612 of the support member 614 may have a larger height and a greater contact surface area than the anterior portion or first support portion 611. A contact surface area of the second support portion 612 that is greater than the contact surface area of the first support portion 611 will contribute to asymmetric loading of the proximal tibiofibular joint which is consistent with the arrangement of the anterior and posterior ligaments 401 and 402. Furthermore, the inner component 614 generally has a concave cross-section and the first and second support portions 611 and 612 meet at a mid-portion of the inner component 614 and the outer regions of the first and second support portions 611 and 612 have a thicker cross-section than the mid-portion thus defining recessed portion 617 and void 619.

Figure 11A:
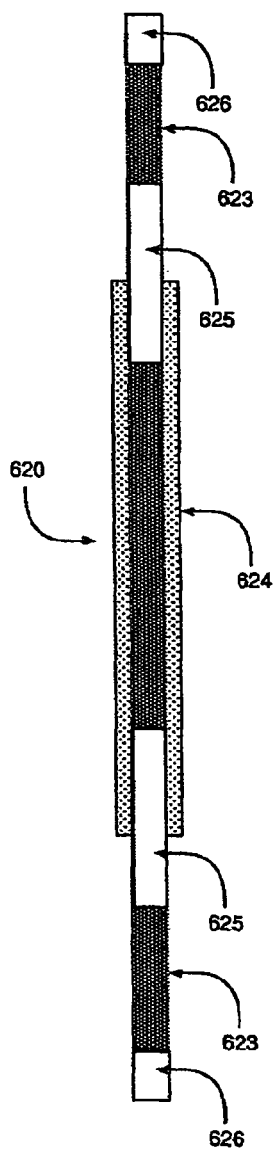
FIG. 11A is a view of the outer or top surface of the securing member for the orthosis of FIG. 8 showing its different components.

The securing member 620 for the orthosis 600 is shown in FIG. 11A. The securing member 620 includes a tensioning portion 623 and a force distribution portion 624. The tensioning portion 623 of the securing member 620 may be made at least partially from cross-woven materials such as nylon or cotton. The use of cross woven materials helps the tensioning portion 623 adapt to the shape of the leg of the wearer in the area associated with the proximal tibiofibular joint 400. Cross woven material helps the tensioning portion 623 of the securing member 620 adapt to the contours of the leg in the area where the orthosis 600 is applied. Since comfort at low tension levels is important to the optimal function of the orthosis 600, cross woven materials that will not lengthen appreciably once tensioned are preferable.

The force distribution portion 624 of the securing member 620 includes the inner or skin surface of the securing member 620. It may be made from foam materials such as closed cell nitrogen filled foams like neoprene. In order to avoid pinching of the flesh, the force distribution portion 624 of securing member 620 may be approximately 50% wider than the tensioning portion 623 of the securing member 620. In order to minimize chafing and irritation to the skin of the wearer, the material used in the force distribution portion 624 of the securing member 620 may be between 4 and 6 millimetres in thickness. The material from which the force distribution portion 624 is made may be bonded to the material of the tensioning portion 623 by using glue or some other suitable bonding means as is commonly known to those skilled in the art. These two portions of the securing member 620 may also be stitched together.

The force distribution portion 624 of the securing member 620 provides a broad distribution of force across the lateral head of the gastrocnemius muscle situated in the posterior aspect of the leg of the wearer due to the increased width of the surface of the force distribution portion 624 in relation to the width of the tensioning portion 623. Accordingly, the relative dimensions of the components of the securing member serve to minimize interference with expansion of the muscle during contraction. Accordingly, the orthosis 600 transfers load to the anterolateral and posterolateral aspects of the proximal fibula in a manner that reduces the application of compression force on the lateral aspect of the proximal fibula. This results in an orthosis that is not only easy to use but very comfortable to wear since the compressive force applied to soft tissue required to control movement of the joint is reduced.

Figure 11B:
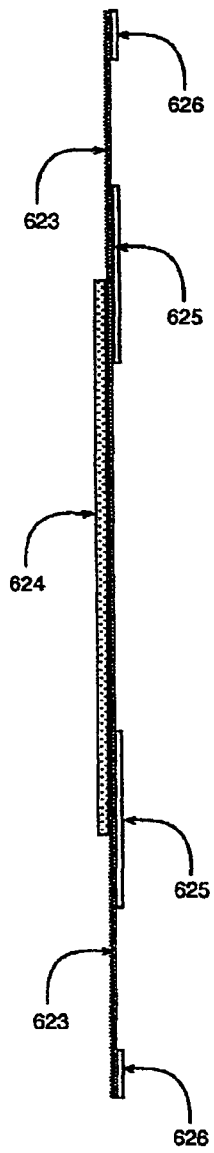
FIG. 11B is a side view of the securing member for the orthosis of FIG. 8 showing its different components.

FIG. 11B shows the side surface or thickness of the securing member 620. In this exemplary embodiment, the securing member 620 may be affixed to outer component 613 of the support member 610 of the orthosis 600 by a closure element or closure means that engage the attachment element 630. In this example, the closure means include hook and loop fasteners such as Velcro™. The hook portion 625 of the fastener has a preferably long length in order to accommodate individuals with varying calf sizes. The loop portion 626 of the attachment element 630 is preferably smaller since this makes it easier to slip this portion between the pin 633 and the outer surface of the outer component 613 of the support member 610 and pull this portion back to the remainder of the securing member 620. Various lengths can be chosen for the hook and loop portions 625 and 626 as well as for the force distribution portion 624 of the securing means 620.

The combination of the neoprene foam in the force distribution portion 624 of the securing member 620 and the viscoelastic gel type matrix pad of the inner component 614 of the support member 610 of the orthosis 600 allow for proper arterial and venous blood circulation as well as for nerve conduction by distributing the force applied to the soft tissue with an adaptive medium at the interface of the orthosis 600 with the soft tissue of the wearer that has properties similar to the soft tissue.

The force distribution portion can have a closed cell foam with a thickness of at least approximately 4 mm. Thinner and/or harder materials may not be as comfortable because of the necessarily harder material of the tensioning portions. Discomfort may prevent proper tensioning of the securing member and should be avoided. Further, this thickness helps the force distribution portion adapt to the contours of the leg in the area where the orthosis 600 is applied.

Figure 11C:
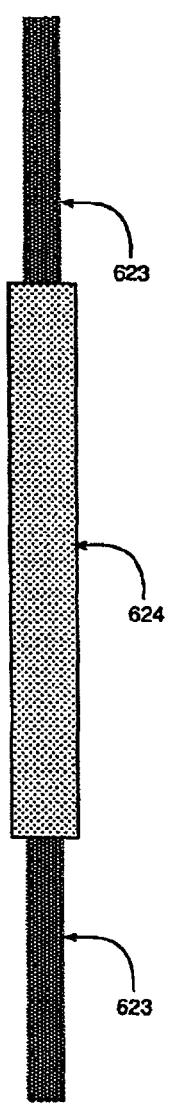
FIG. 11C is a view of the inner or skin surface of the securing member for the orthosis of FIG. 8 showing its different components.

FIG. 11C shows the skin contact side of the securing member 620 with the force distribution portion shown at 624 and the tensioning portion shown at 623.

In use, an end of the securing member 620 is slipped between the outer face of the outer component 613 of the support member 610 and the inner surface of the pin 633 towards the middle of the support member 610 of the orthosis 600. An appropriate amount of the securing member 620 is preferably drawn between the pin 633 and the outer component 613 to obtain the approximate length needed to fit the circumference of the leg of the wearer in the area associated with the proximal tibiofibular joint 400. The end of the securing member 620 is then looped backwards over the top of the pin 633 so that the hook portion 625 of the securing member 620 may be affixed to the loop portion 626 of the securing member 620. The loose end of the securing member 620 is then wrapped about the leg of the wearer and inserted under pin 633 on the other end of the support member 610 of the orthosis 600 in the fashion just described. The loose end of the securing member 620 is then drawn around the pin 633 so as to tension the support member 610 of the orthosis 600 circumferentially around the leg of the wearer.

Figure 12:
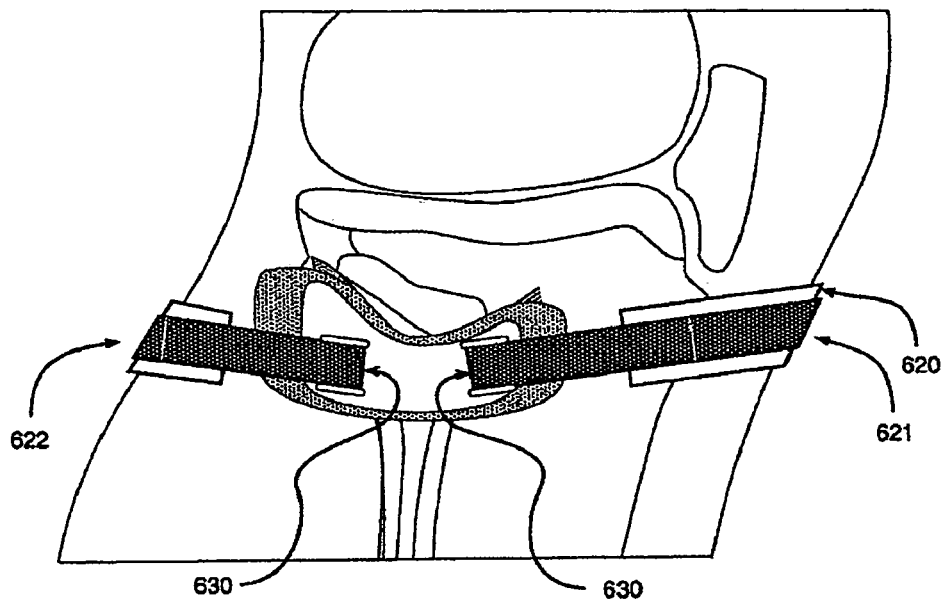
FIG. 12 is a lateral sagittal plane view of the orthosis of FIG. 8 placed on the right tibiofibular joint of a wearer.
Figure 13:
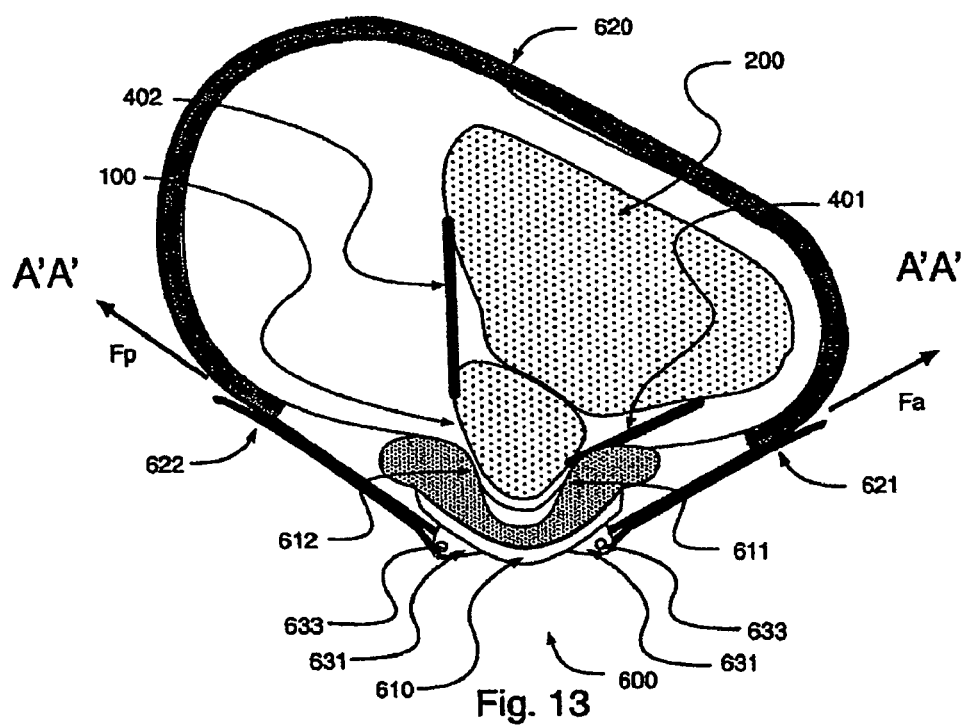
FIG. 13 is a proximal coronal plane sectional view of the right proximal tibiofibular joint similar to that shown in FIG. 4 along with an associated section of the orthosis embodiment of FIG. 8.

Prior to tensioning the securing member 620, the support member 610 of the orthosis 600 is properly positioned on the proximal tibiofibular (TF) joint 400 so that the first support portion 611 is situated anteriorly with respect to the TF joint 400 and the second support portion 612 is situated posteriorly with respect to the TF joint 400 and the vertical position of the support portions 611 and 612 are such that contact is made with the shaded portions of the TF joint 400 as shown in FIG. 5. In one instance, the second support portion 612 may first be positioned behind the fibular head 101 at the approximate level of the neck 103 of the fibula 100. The support member 610 of the orthosis 600 may then be shifted proximally to seat the first support portion 611 of the support member 610 of the orthosis 600 on the head 101 of the proximal fibula 100. The vertical center of the support member 610 of the orthosis 600 may then be aligned with the lateral aspect of the proximal fibula 100. FIGS. 12 and 13 show the orthosis 600 correctly positioned on the proximal tibiofibular joint 400 of the right leg of a wearer.

When the support member 610 of the orthosis 600 is properly positioned on the proximal tibiofibular joint 400 and tensioned about the leg of the wearer with the securing member 620, the securing member 620 should feel firm but comfortable on the leg of the wearer. There should be enough tension in the securing member 620 to prevent the support member 610 from migrating proximally, distally or rotationally on the leg of the wearer in use or if the orthosis 600 is tugged upon. There should not be any distal pain, tingling, numbness or swelling. Further, when properly fit to the wearer, the orthosis 600 should minimize the compression force applied to the hard and soft tissues on and adjacent to the proximal tibiofibular joint.

Pathologies arising from trauma to the proximal tibiofibular joint 400 typically compromise the integrity of the joint asymmetrically in terms of the role of its anterior and posterior ligaments 401 and 402. Trauma of this nature tends to disturb the synergy of the anterior and posterior ligaments 401 and 402 responsible for recentering the joint in its neutral position from translations and rotations. Since the posterior ligament 402 is weaker than the anterior ligament 401, trauma to the proximal tibiofibular joint 400 will often manifest itself in the posterior ligament 402 resulting in a partial or complete rupture.

Where pathologies resulting in asymmetric instability of the proximal tibiofibular joint 400 are present, the individual can be provided with an adjustment means or adjustment element to alter the mechanics of the orthosis 500, 600 so that the forces applied by the support member 510, 610 of the orthosis 500, 600 to the anterior aspect 104 and posterior aspect 105 of the proximal fibula 100 serve to at least partially compensate for the asymmetric instability of the proximal tibiofibular joint 400.

Figure 14:
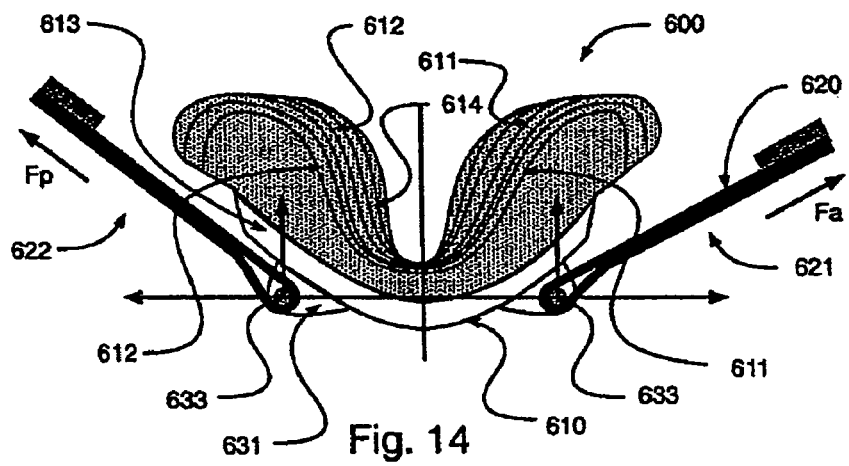
FIG. 14 is a partial proximal coronal plane view of the orthosis similar to that shown in FIG. 8 with the addition of arrows to show the vectors of the forces typically applied to the proximal tibiofibular joint when the orthosis is worn.

Referring now to FIG. 14, shown therein is a partial top view of the orthosis 600 in which the upper flange 631 has been removed in order to show the fixation of the ends of the securing member 620 with pins 633. The pins 633 are located in symmetric positions in corresponding holes in the flanges 631. Arrows emanating from the pins 633 show the approximate magnitude of the components of shear (horizontal to the TF joint 400) and compressive (vertical to the TF joint) forces for each of the resultant forces Fa and Fp applied to the pins 633 by the securing member 620. These forces are transferred to the first and second portions 611 and 612 of the support member 610 primarily as shear forces due to the angular relationship of the planes of the anterior and posterior aspects 621 and 622 of the securing member 620 and the planes of the first and second support portions 611 and 612 of support member 610.

Since the position of the attachment element 630 on the support member 610 has an effect on the force that is applied to the TF joint 400, the mechanics of the orthosis 600 can be altered by providing means to affix the anterior and posterior aspects of the securing member 620 in different locations on the outer component 613 of the support member 610. The means to alter the mechanics of orthosis 600 in this manner enables asymmetric loading of the proximal tibiofibular joint In one exemplary implementation, the attachment member 630 may include at least one flange and a pin or post. In this case, the pin or post may have a bulbous end that prevents the ends of the securing member 620 from slipping off of the attachment member 630 once the loop and hook portions 626 and 625 have been attached to one another. In this implementation the mechanics of the orthosis 600 can be altered by either locating the flange or the pin/post in different positions on the support member 610 of the orthosis 600 since this will have an effect on the forces applied to the pins 633 by the securing member 620.

In another exemplary implementation the attachment member may include at least one flange with at least two mounting positions for a pin or post. Once again if one flange is used then the pins/posts may have a bulbous end to keep the securing member in place. In this exemplary implementation, shifting the location of the pins/posts 633 in either the anterior or posterior flange so that the pins/posts 633 are more inboard or outboard (i.e. closer or further away) from the center of the outer component 613 of the support member 610 will alter the moment of force applied to the support member 610 by the securing member 620. Locating the pins/posts 633 so that they are symmetrically located towards the outboard position of the outer component 613 of the support member 610 decreases the moment of force applied to the proximal fibula 100 by the support member 610. Locating the pins/posts 633 so that they are symmetrically located towards the inboard position of the outer component 613 of the support member 610 increases the moment of force applied on the proximal fibula 100 by the support member 610. Further, locating the pins/posts 633 so that they are asymmetrically located on the outer component 613 of the support member 610 will result in approximately asymmetric moments of force applied to the proximal fibula 100 by the support member 610 of the orthosis 600.

In terms of acting as quasi-ligaments, the anterior aspect 621 of the securing member 620 in combination with the transfer of force at the posterior aspect 612 of the support member 610 acts as the anterior ligament 401 of the proximal tibiofibular joint 400. The posterior aspect 622 of the securing member 620 operates in a corresponding fashion. Accordingly, to alter the nature of forces transferred to the proximal fibula 100 by the support member 610, one may alter the location of the connection of the securing member 620 to the support member 610. For example, if some form of pathology has compromised the anterior ligament 401 of the proximal tibiofibular joint 400, the pathology can be at least partially compensated for by increasing the force transferred by the anterior portion 621 of the securing member 620 to the second support portion 612 of the support member 610. This is done by altering the mechanics on the anterior aspect of the support member 610 in a manner that increases the shear force applied to the anterior portion 611 of the support member 610 by the first support portion 611 and the anterior aspect 621 of the securing member 620. This will increase the force that acts to resist posterior translation and internal rotation in a manner similar to the anterior ligament 401. Where some form of pathology has compromised the posterior ligament 402 of the proximal tibiofibular joint 400, the force transferred by the second portion 612 of the support member 610 and the posterior portion 622 of the securing band 620 may be similarly altered.

Thus the ability to alter the position of the attachment element 630 for the anterior and posterior aspects 621 and 622 of the securing band 620 on the outer component 613 of the support member 610 provides different forces to the TF joint 400 thereby enabling the mechanics of the orthosis 600 to be altered so as to at least partially compensate for intrinsic asymmetric instability of the proximal TF joint 400 for various pathologies.

Figure 15:
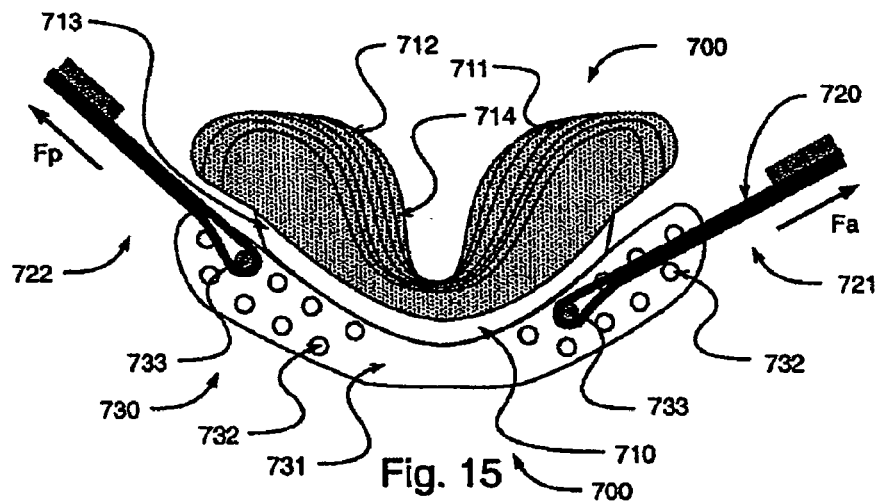
FIG. 15 is a partial proximal coronal plane view of an exemplary alternative embodiment of an orthosis with an adjustment element for varying the force applied to the proximal tibiofibular joint.

FIG. 15 shows an exemplary alternative embodiment of an orthosis 700 with support member 710, first and second support portions 711 and 712 and outer component 713 and inner component 714 with an attachment member 730 including upper and lower flanges 731 with a plurality of apertures situated at the anterior and posterior aspects of the flanges. Alternatively, a pair of anterior and posterior flanges may be used for the lower and upper flanges. In another alternative, only one pair of anterior and posterior flanges may be used with pins/posts with bulbous heads. The flanges 731 are expanded in size and include a plurality of holes 732 for providing multiple locations with which to place a pin/post 733 and hence apply a variety of different forces to the TF joint 400. The top flange 731 is not shown in order to show the plurality of positions at which the ends of the securing member 720 may be fixed with a pin/post 733. Vacant apertures are typically labeled as 732, two of which are labeled for example.

Figure 16:
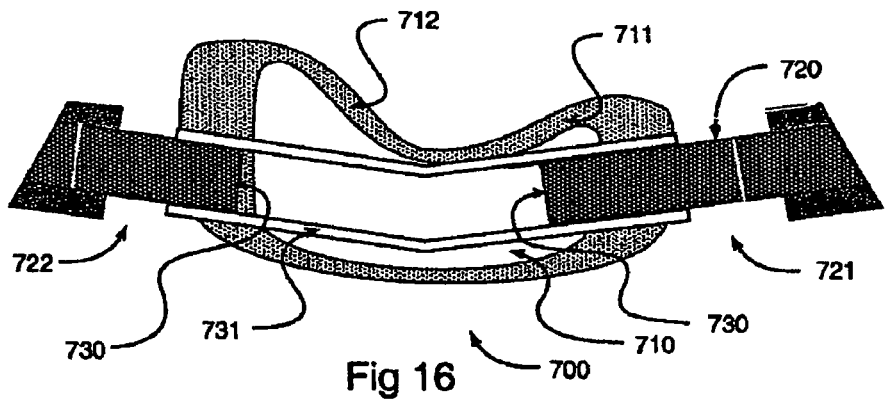
FIG. 16 is a lateral sagittal plane elevation view of the orthosis of FIG. 15.

The anterior aspect 721 of the securing member 720 is shown affixed to pin 733 located in the same position relative to the outer component 713 of the support member 710 as was shown in FIG. 14. However, the posterior aspect 722 of the securing member 720 is shown affixed to the posterior pin 733 located in a position that is outboard compared to the attachment location shown in FIG. 14. With the pins 733 configured in this manner, the support member 710 of the orthosis will apply a greater moment of force to the posterolateral aspect 108 of the proximal fibula 100 than to the anterolateral aspect 109 of the proximal fibula 100. FIG. 16 shows a lateral view of the outer component 713 of the support member 710 of the orthosis 700 with expanded flanges 731 and with asymmetric location of pins/posts 733 for the anterior and posterior aspects 721 and 722 of the securing member 720.

Figure 17:
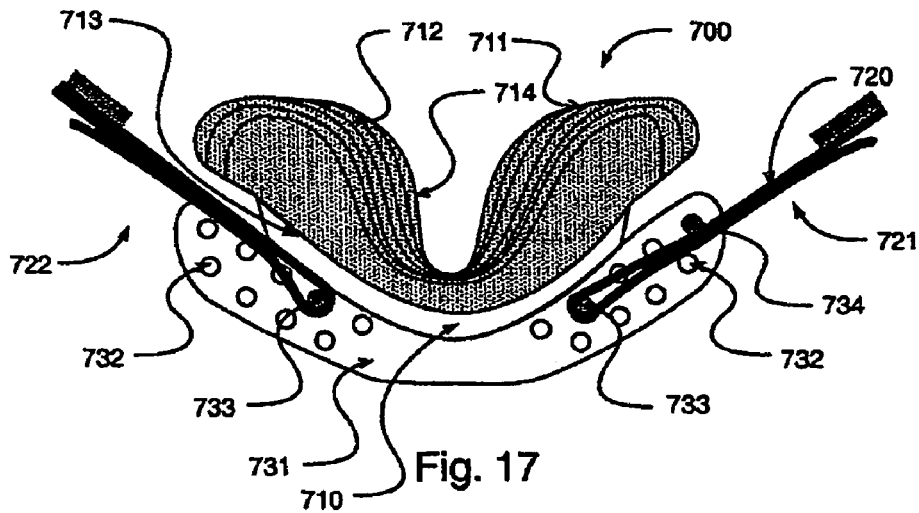
FIG. 17 is a partial proximal coronal plane view of the orthosis of FIG. 15 with one exemplary configuration of the adjustment element.
Figure 18:
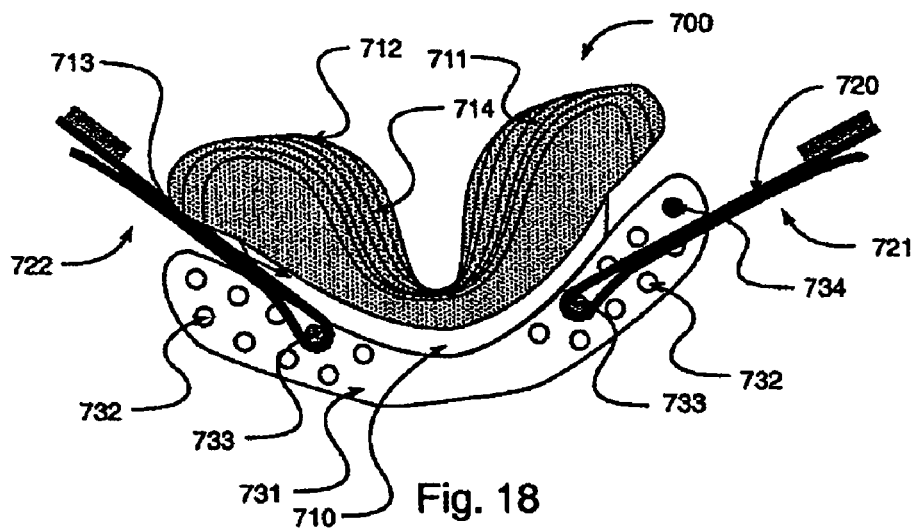
FIG. 18 is a partial proximal coronal plane view of the orthosis with the adjustment element in the configuration of FIG. 17 showing external rotation of the orthosis that occurs during external rotation of the proximal tibiofibular joint.
Figure 19:
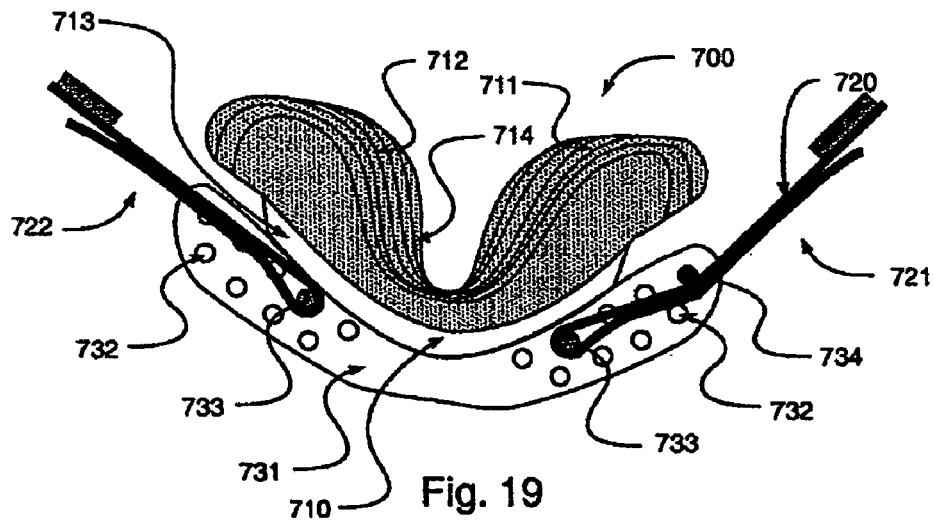
FIG. 19 is a partial proximal coronal plane view of the orthosis with the adjustment element in the configuration of FIG. 17 showing an internal rotation of the orthosis that occurs during internal rotation of the proximal tibiofibular joint.

FIG. 17 shows the anterior and posterior aspects 721 and 722 of the securing member 720 affixed to pins 733 located in the same symmetrical locations as pins 633 in FIG. 14 except that a resistance member, in this case resistance pin 734, has been fit to an outboard pin location on the anterior aspect of the orthosis 700. Resistance pin 734 acts to effectively shorten the anterior aspect 721 of the securing member 720 during external rotation (clockwise as shown in FIG. 19) of the support member 710 of the orthosis 700. This configuration increases the moment of force applied to the anterolateral aspect 107 of the proximal fibula 100 during external rotation of the support member 710 of the orthosis 700. FIG. 18 shows that rotating support member 710 of the orthosis 700 internally (counterclockwise in FIG. 18) has no effect on the moment of force applied to the proximal fibula 100 because the anterior portion 721 of the securing member 720 will only contact resistance pin 734 during external rotation of support member 710.

FIG. 19 shows how rotating the support member 710 of the orthosis 700 externally engages the anterior portion 721 of the securing member 720 with resistance pin 734 causing the anterior portion 721 of the securing member 720 to effectively shorten in length thereby increasing the re-centering force applied to the anterolateral aspect 107 of the support member 710 of orthosis 700. In situations where the anterior ligament 401 of the proximal tibiofibular joint 400 is compromised due to some form of pathology, resistance pin 734 may be similarly fit on the posterior portion 712 of the support member 710 of the orthosis 700.

Figure 20:
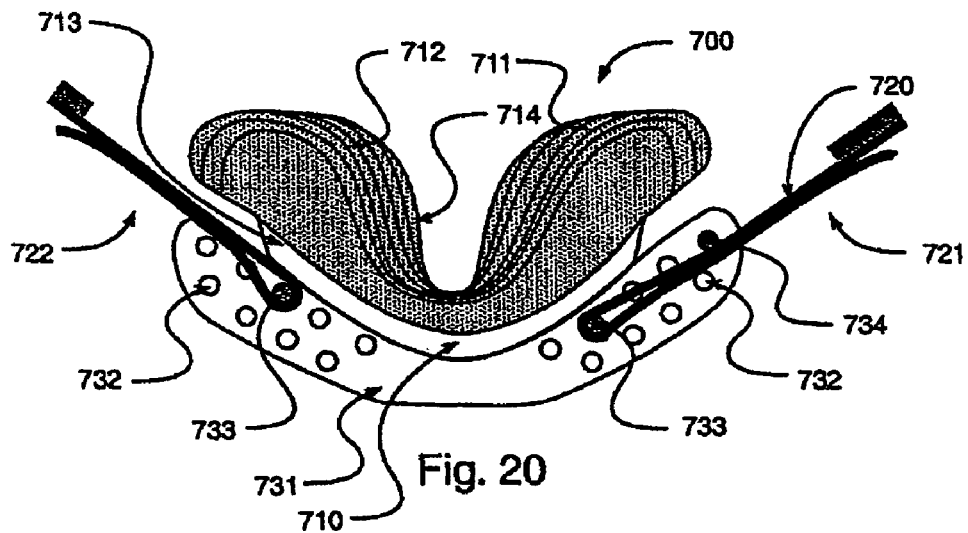
FIG. 20 is a partial proximal coronal plane view of the orthosis of FIG. 15 with an alternate configuration for the adjustment element.

FIG. 20 is the same configuration as FIG. 17 with the resistance pin 734 fit in an outboard position on the anterior portion of the support member 710 except that the posterior pin 733 on the posterior portion of the support member 710 has been moved more outboard so as to create asymmetrical fixations of the anterior and posterior portions 721 and 722 of the securing member 720 on the outer component 713 of the support member 710 of the orthosis 700. This configuration serves to further increase the differential of the moment of force applied to the proximal tibiofibular joint 400 by the orthosis 700.

Figure 21:
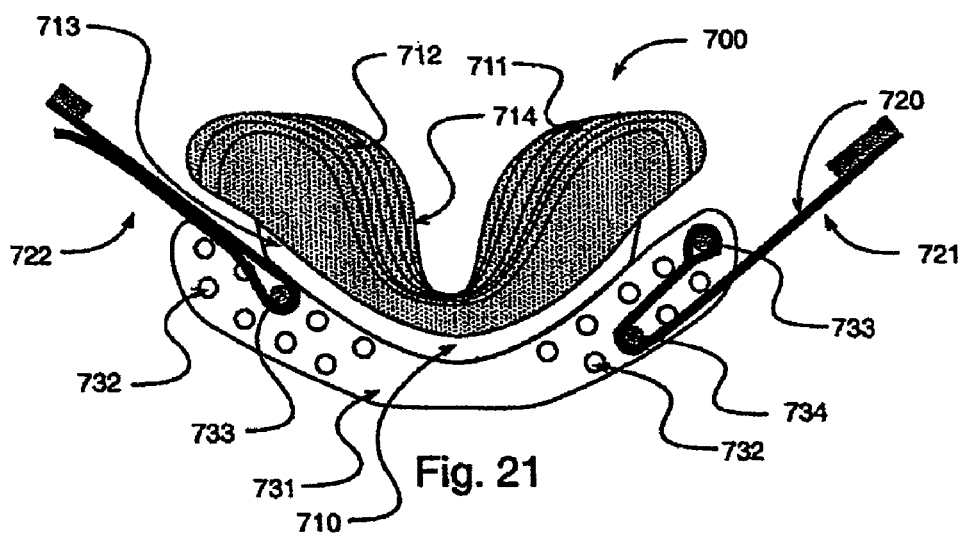
FIG. 21 is a partial proximal coronal plane view of the orthosis of FIG. 15 with another alternative configuration for the adjustment element.

In some forms of pathology of the proximal tibiofibular joint 400 involving asymmetric instability in which either the anterior or posterior ligaments 401 or 402 have been compromised, it may be advantageous to have the moment of force applied to the proximal tibiofibular joint 400 by the orthosis decrease on the same side as the stronger ligament. It is also possible to mount the resistance pin inboard of either the posterior or anterior pins 733 and have the securing member 720 loop around the resistance pin where it reverses itself. The effect of this arrangement is to cause securing member 720 to effectively lengthen during rotation toward the same side as this arrangement thereby reducing the tension of the securing member 720 and the moment of force applied to the associated side of the proximal tibiofibular joint 400. FIG. 21 shows this arrangement. Securing member 720 has been altered so that one end has a closed loop instead of hook and loop fasteners 625 and 626. The pin/post 733 on the outboard side of one end of support member 710 is removed from flanges 731. The closed loop end of support member 720 is inserted between flanges 731 and the pin/post 733 is then re-inserted into flanges 731 through the closed loop in the end of securing member 720. A resistance pin 734 is then mounted on the same side of support member 710 inboard of pin/post 733. The unfixed end of securing member 720 is then inserted between resistance pin 734 and the outer component 731 of support member 720. As an alternative method, once the closed loop end of securing member 720 is fixed to pin 733 of support member 720, the securing member 720 can be directed inboard of its fixation at pin/post 733 and placed between flanges 731 so that it is positioned between the outer component 713 of support member 710 and the apertures 732 in flanges 731 where resistance pin 734 is to be inserted. When securing member 720 is in position at this location, resistance pin 734 is inserted in the apertures 732 in flanges 731 through the closed loop in the end of securing member 720. The unfixed end of securing member 720 is then directed back towards its fixed end on support member 710 and then wrapped about the calf of the wearer. The loop end 626 of the hook and loop fasteners 625, 626 on the loose end is then inserted between the pin/post 733 and the outer component 731 of support member 710. The securing member 720 is then tensioned as previously described.

Figure 22:
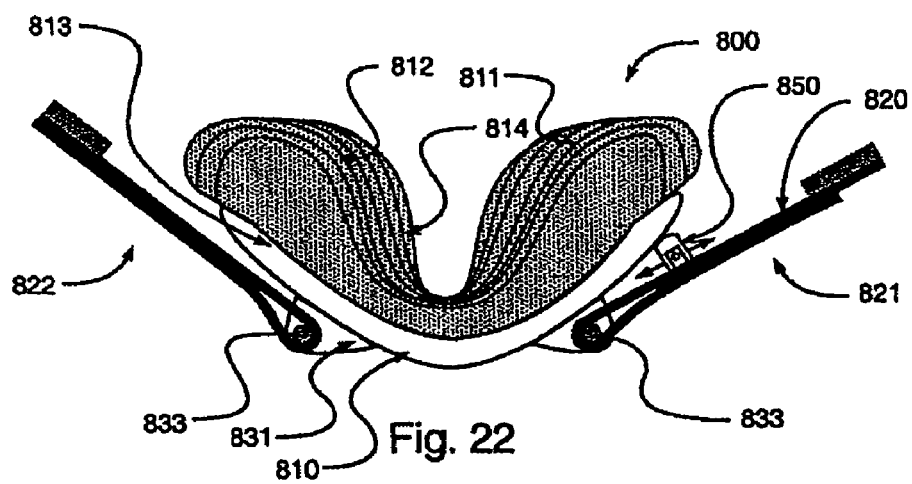
FIG. 22 is a partial proximal coronal plane view of another alternate embodiment of an orthosis having a pivot element.

FIG. 22 shows another alternative embodiment of an orthosis 800 in which the resistance member is a removable pivot element 850. In this example, the removable pivot element 850 is fit to the anterior aspect 821 of the securing member 820. However, the removable pivot element 850 may also be fit to the posterior aspect 822 of the securing member 820. When the removable pivot element 850 is mounted on the securing member 820 so as to bear against the outer component 813 of the support member 810, the pivot element 850 has a similar effect on the mechanics of the orthosis 800 as the resistance pin 734. The "outboard" position of the pivot element 850 may be continuously adjustable on the securing member 820 within the physical outer limits of the outer component 813 of the support member 810. Teeth may be provided on the pivot element 850 at the interface with the securing member 820 to fix the position of the pivot element 850 on the support member 820.

Figures 23A, 23B:
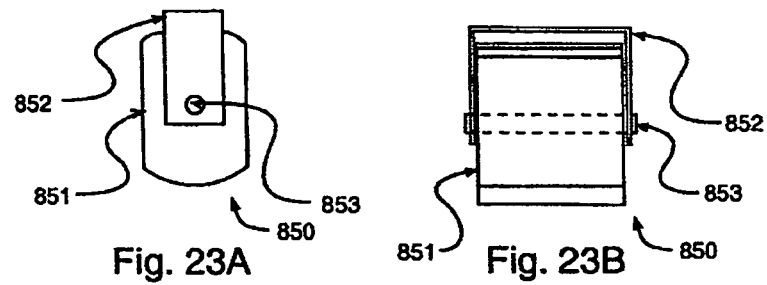
FIG. 23A is a side elevation of the pivot element of FIG. 21.
FIG. 23B is a front view of the pivot element of FIG. 21.

FIGS. 23A and 23B show side and front elevational views, respectively, of the pivot element 850. The pivot element 850 includes a body 851 having a channel, a hinged member 852, and a pivot pin 853. The hinged member 852 includes a frame with two opposing apertures. The frame is shaped to partially encircle the circumference of the body 851. The pivot pin 853 is disposed within the channel of the body 851 and engages the two apertures of the hinged member 852. The hinged member 852 can pivot with respect to the body 851 about the pivot pin 853. The pivot element 850 further includes a locking mechanism (not shown) located at one of the body and the hinged member for configuring the pivot means In a locked position. The body 851 may include teeth (not shown) which act as the locking mechanism to lock the hinged member 852 in place. Alternatively, other suitable means may be used for the locking mechanism and the locking mechanism may be located on the lower portion of the hinged element 852. Alternatively, the locking mechanism may include providing an appropriate sized gap between the hinged element 852 and the body 851 so that when the pivot element 850 is in the locked position, a friction fit is made with the securing member 820.

Figure 24:
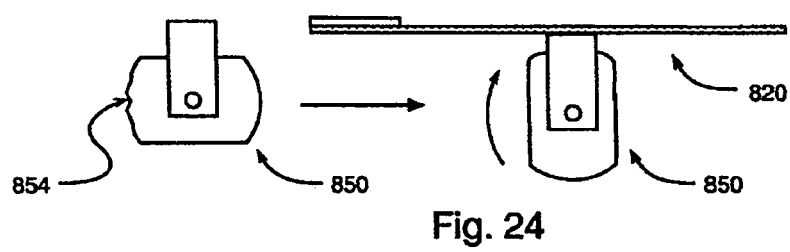
FIG. 24 illustrates how the pivot element of FIG. 21 is fit onto a securing member of the orthosis of FIG. 21; and, FIG. 25 is a proximal coronal plane view of another alternative embodiment of the orthosis.

FIG. 24 shows the operation of the pivot 850. The hinged member 852 of the pivot 850 is rotated to the open position so that the pivot 850 can be inserted at one end of the securing member 820. When the pivot 850 is at the desired location on the securing member 820, the hinged member 852 is rotated into the closed position. The locking mechanism is then used to lock the pivot 850 in place on the securing member 820 by clamping the securing member 820 between the body 851 of the pivot 850 and the frame 852. Accordingly, in use, the pivot means 850 is configured in an unlocked position, slid into place on the securing member 820 and then configured into the locked position by rotating the body 851 so that the locking mechanism is engaged to hold a portion of the securing member 820 between the body 851 and the hinged member 852.

Figure 25:
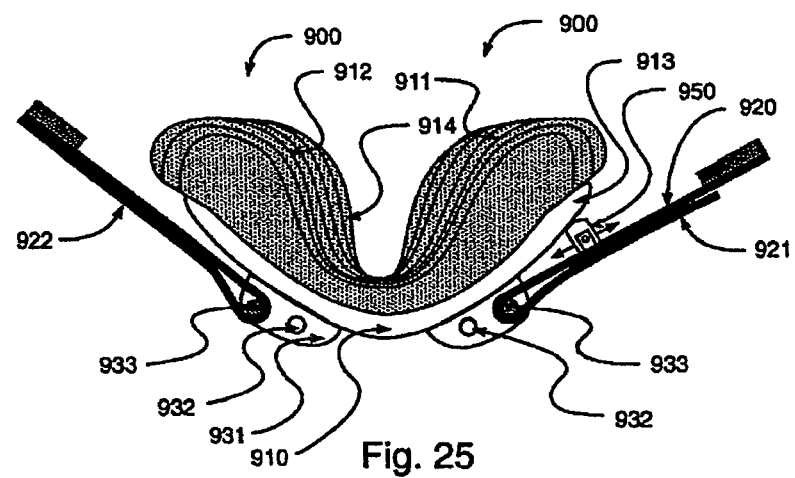

FIG. 25 shows another alternative embodiment of an orthosis 900 in accordance with the invention. The outer component 913 of the support member 910 includes a flange 931 with two sets of holes 932 to receive pins or posts 933. The inner component 914 of the support member 910 includes first and second support portions 911 and 912. The orthosis 900 also includes a pivot member 950. This configuration creates mechanics for the orthosis 900 that are similar to the configuration shown in FIG. 20. In this example, the removable pivot 950 is fit to the anterior aspect 921 of the securing member 920. Pivot 950 can also be fit to the posterior aspect 922 of support member 910. It should be understood that the anterior and posterior flanges may be replaced with a single flange. Further, there may be a variation in which only an upper or lower pair of flanges are used in which case there is preferably a bulbous end on the pin or post to hold the securing member 920 in place during use.

It should be understood that the various embodiments of the orthosis described herein can be made using commonly available materials and processes that are cost-effective. Accordingly, the various embodiments of the orthosis described herein is economical to manufacture. Further, it should be understood that the various embodiments of the orthosis shown herein which provide an adjustable attachment element on the support member allow one to alter the moments of force applied by the orthosis. Further, the various different adjustable attachment elements shown herein allow one to alter the moments of force applied by the orthosis on the anterior and posterior aspects of the proximal tibiofibular joint independently of each other. In addition, for the various embodiments of the orthosis described herein, at least some of the components of the orthosis can be replaced with different components in order to individualize the orthosis to the requirements of the user. By example, securing bands of different lengths and/or physical characteristics can be easily fit to the support member in order to adapt the orthosis to the individual requirements of the wearer.

It should be understood that various modifications can be made to the embodiments described and illustrated herein, without departing from these embodiments, the scope of which is defined in the appended claims. It should further be understood that the term orthopaedic can also be used to refer to the various orthoses that have been described in this application.

The invention claimed is:

1. An orthopaedic appliance for bracing and supporting a proximal tibiofibular joint of a leg, the orthopaedic appliance comprising:
   a) an at least semi-rigid support member having a first support portion and a second support portion each protruding from a back side of the support member and a recessed portion disposed on the back side between said first support portion and said second support portion, wherein said first support portion and said second support portion are each adapted to contact the leg to support the anterolateral and posterolateral aspects, respectively, of the head and neck of a proximal fibula, and wherein said recessed portion defines a void that is adapted to receive the lateral aspect of the head and neck of the proximal fibula to prevent excessive compressive forces being applied thereto; and
   b) a securing member connected to the support member for securing the support member to brace and support the proximal tibiofibular joint, wherein the first support portion of the support member applies a posteromedial force to the anterolateral aspect of the proximal fibula and the second support portion of the support member applies an anteromedial force to the posterolateral aspect of the proximal fibula.

2. The orthopaedic appliance of claim 1, wherein the second support portion has a contact surface area that is larger than a contact surface area of the first support portion.

3. The orthopaedic appliance of claim 1, wherein the securing member comprises a band having a force distribution portion and at least one tensioning portion, the force distribution portion being wider than the at least one tensioning portion.

4. The orthopaedic appliance of claim 3, wherein the band is at least partially made from a cross-woven material.

5. The orthopaedic appliance of claim 3, wherein the force distribution portion comprises a closed cell foam having a thickness of at least approximately 4 mm 6. The orthopaedic appliance of claim 1, wherein said support member comprises an outer component and an inner component and wherein the outer component is made from a more rigid material than the inner component.

7. The orthopaedic appliance of claim 6, wherein the inner and outer components have a concave upper surface and a convex lower surface, with the ends of the inner and outer components extending upwardly.

8. The orthopaedic appliance of claim 6, wherein the posterior region of the inner and outer components extends further upwards than the anterior region of the inner and outer components.

9. The orthopaedic appliance of claim 6, wherein the inner component generally has a concave cross-section.

10. The orthopaedic appliance of claim 6, wherein the inner component comprises a viscoelastic matrix material.

11. An orthopaedic appliance for bracing and supporting a proximal tibiofibular joint, the orthopaedic appliance comprising:
   a) an at least semi-rigid support member having a first support portion and a second support portion corresponding generally to the anterolateral and posterolateral aspects, respectively, of the head and neck of a proximal fibula; and
   b) a securing member connected to the support member for securing the support member to brace and support the proximal tibiofibular joint, wherein the first support portion of the support member applies a posteromedial force to the anterolateral aspect of the proximal fibula and the second support portion of the support member applies an anteromedial force to the posterolateral aspect of the proximal fibula, and
   c) an attachment element located on the support member and comprising a pair of upper and lower flanges, each pair having at least one aperture and a pin, wherein two end portions of the securing member individually form a loop around one of the pins for maintaining the securing member in position during use.

12. The orthopaedic appliance of claim 11, wherein the upper and lower flanges comprise a plurality of holes for allowing the pins to be placed in an antisymmetric fashion for adjusting the forces applied to the joint by the first and second support portions in combination with the securing member in use.

13. The orthopaedic appliance of claim 12, wherein the attachment element further comprises a resistance member placed closer to the anterior edge, posterior edge or midline of the support member in comparison to the location of the pins, for further adjusting the forces applied to the joint by the first and second support portions in combination with the securing member in use.

14. The orthopaedic appliance of claim 13, wherein the resistance member comprises one of a pin and a post.

15. The orthopaedic appliance of claim 12, wherein the resistance member comprises a pivot element including:
   a) a body having a channel;
   b) a hinged member having a frame with two opposing apertures, the frame being shaped to partially encircle the circumference of the body;
   c) a pin disposed within the channel of the body and engaging the two apertures of the hinged member; and,
   d) a locking mechanism located at one of the body and the hinged member for configuring the pivot element in a locked position;
   wherein, in use, the pivot element is configured in an unlocked position, slid into place on the securing member and then placed configured into the locked position by rotating the body so that the locking mechanism is engaged to hold a portion of the securing member between the body and the hinged member.

16. The orthopaedic appliance of claim 11, wherein said support member includes a recessed portion defining a void between said first support portion and said second support portion adapted to receive the lateral aspect of the proximal fibula to prevent excessive compressive force being applied thereto.

17. An orthopaedic appliance for bracing and supporting a proximal tibiofibular joint of a leg, the orthopaedic appliance comprising:
   a) an at least semi-rigid support member having a first support portion and a second support portion each protruding from a back side of the support member and a recessed portion disposed on the back side between said first support portion and said second support portion, wherein said first support portion and said second support portion are each adapted to contact the leg to support the anterolateral and posterolateral aspects, respectively, of the head and neck of a proximal fibula, and wherein said recessed portion defines a void that is adapted to receive the lateral aspect of the head and neck of the proximal fibula to prevent excessive compressive forces being applied thereto; and
   b) a securing member connected to the support member for securing the support member to brace and support the proximal tibiofibular joint, wherein the first support portion of the support member applies a posteromedial force to the anterolateral aspect of the proximal fibula and the second support portion of the support member applies an anteromedial force to the posterolateral aspect of the proximal fibula; and an attachment element located on the support member, said attachment element having a plurality of selectable attachment points adapted for receiving said securing member to adjust the forces applied to the joint by the first and second support portions.

18. The orthopaedic appliance of claim 17 wherein said second support portion of said support member has a contact surface that is larger than the contact surface area for the first support portion of said support member.

19. The orthopaedic appliance of claim 17, wherein the securing member comprises a band having a force distribution portion and at least one tensioning portion, the force distribution portion being wider than the at least one tensioning portion.

20. An orthopaedic appliance as claimed in claim 17 wherein the support member comprises an outer component and an inner component and wherein the outer component is made from a more rigid material than the inner component.

* * * * *